United States Patent [19]
Merten et al.

[11] 3,939,122
[45] Feb. 17, 1976

[54] PROCESS FOR THE PREPARATION OF COMPOUNDS WHICH CONTAIN HYDANTOIN RINGS

[75] Inventors: Rudolf Merten, Leverkusen; Jurgen Lewalter, Cologne; Wilfried Zecher, Leverkusen, all of Germany

[73] Assignee: Bayer Aktiengesellschaft, Germany

[22] Filed: Aug. 1, 1974

[21] Appl. No.: 493,521

Related U.S. Application Data

[63] Continuation-in-part of Ser. No. 457,853, April 4, 1974, abandoned.

[30] Foreign Application Priority Data

Apr. 11, 1973 Germany............................ 2318205

[52] U.S. Cl.. 260/77.5 R; 260/77.5 AT; 260/309.5; 260/DIG. 34
[51] Int. Cl.².......................................... C08G 18/08
[58] Field of Search................ 260/77.5 R, DIG. 34

[56] References Cited
UNITED STATES PATENTS

| | | | |
|---|---|---|---|
| 2,829,157 | 4/1958 | McKinney.................... | 260/DIG. 34 |
| 3,296,208 | 1/1967 | Rogers......................... | 260/DIG. 34 |
| 3,397,253 | 8/1968 | Merten et al.................. | 260/DIG. 34 |
| 3,642,524 | 2/1972 | Merten et al.................. | 260/DIG. 34 |
| 3,676,455 | 7/1972 | Haug et al..................... | 260/DIG. 34 |

Primary Examiner—H. S. Cockeram
Attorney, Agent, or Firm—Connolly and Hutz

[57] ABSTRACT

A process for preparing compounds containing hydantoin groups, wherein compounds which contain isocyanate or isothiocyanate groups are reacted with compounds which contain at least one, preferably two α-halocarboxylic acid amide groups or one α, α'-dihalodicarboxylic acid diamide group.

10 Claims, No Drawings

PROCESS FOR THE PREPARATION OF COMPOUNDS WHICH CONTAIN HYDANTOIN RINGS

This is a continutation-in-part of application Ser. No. 457,853, filed Apr. 4, 1974, and now abandoned.

It is known to prepare polyhydantoins by reacting glycine ester derivatives which are at least difunctional with polyisocyanates (see French Patent Specification No. 1,484,694). This method of forming polyhydantoins can be represented by the following schematic and very simplified reaction equation:

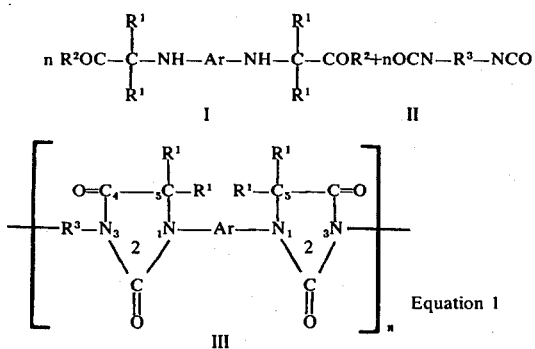

Equation 1

In this reaction equation, the symbols $R^1$ represent independently of each other, hydrogen or an alkyl radical preferably containing 1 to 4 carbon atoms, $R^2$ represents hydroxyl, amino, alkylamino, dialkylamino, alkoxy or aroxy, the alkyl radical preferably containing 1 to 4 carbon atoms and the aryl radical preferably 6 to 10 carbon atoms, Ar denotes an aromatic radical and $R^3$ denotes the organic residue of a diisocyanate.

The reaction may also be carried out with polyfunctional starting materials, i.e. glycine ester derivatives which have more than two glycine ester functions and polyisocyanates which contain more than two isocyanate groups. In that case, branched molecules are formed.

This invention relates to a process for preparing compounds containing hydantoin groups, wherein compounds which contain isocyanate or isothiocyanate groups are reacted with compounds which contain at least one, preferably two, α-halocarboxylic acid amide groups or one α, α'-dihalodicarboxylic acid diamide group or derivatives thereof.

The basic reactions which are capable of taking place in such a process are illustrated by equations 2 and 3 in which a diisocyanate is used as example.

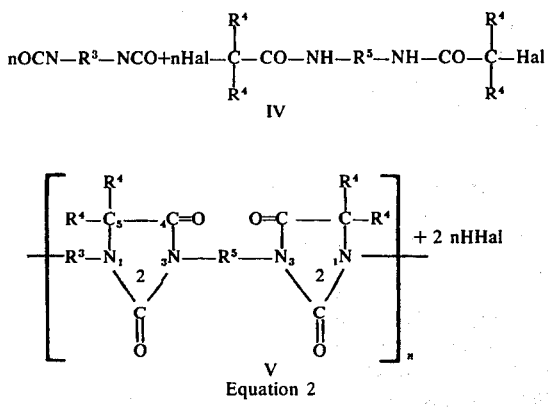

Equation 2

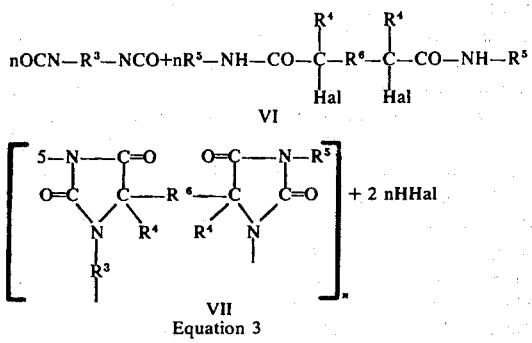

Equation 3

The process may in principle be carried out with any known compounds which contain iso(thio)cyanate groups. If monoiso(thio)cyanates and a compound which contains only one α-halocarbonamide group are used, then compounds with only one hydantoin ring are formed. On the other hand polyiso(thio)cyanates and compounds which contain several α-halocarbonamide groups produce linear or branched, oligomeric or even polymeric substances, depending on the proportions in which the reactants are employed, and these substances contain hydantoin rings as connecting members. In such cases, the chain is continued by way of the N-atoms in the 1-3-3-1 position of the resulting hydantoin rings when di- and polyiso(thio)cyanates are reacted with α-halocarboxylic acid amides which can be prepared from α-halocarboxylic acid of formula VIII and di- or poly-amines of formula IX, whereas when mono- or polyfunctional α-halocarboxylic acid amides which can be obtained by condensing compounds which contain several α-halocarboxylic acid groups of formula XI with monoamines and polyamines, preferably with monoamines of formula IX are used, then the chain is also continued via the carbon atoms in the 5-position of the hydantoin ring. These various forms of cross-linking may be carried out separately or in combination with each other to produce high molecular weight cross-linked substances. The stoichiometric reactions represented in equations 2 and 3 between a diisocyanate and the two difunctional α-halocarboxylic acid amides of formulae IV and VI serves only as example of the synthesis of linear polymers.

Suitable mono- and polyiso(thio)cyanates for the process are compounds of the general formulae

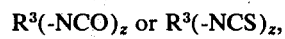

X in which $R^3$ represents an optionally substituted aliphatic radical containing 1 – 20 carbon atoms, an optionally substituted aromatic radical containing 5 – 12 carbon atoms, a cycloaliphatic radical containing 5 – 12 carbon atoms, an aliphatic-aromatic radical containing 6 – 20 carbon atoms and an aromatic or cycloaliphatic heterocyclic radical which contains or is substituted by hetero atoms such as N, O or S and has 5 – 12 ring atoms. Aliphatic radicals which contain 2 to 6 carbon atoms, phenyl-, tolyl-, naphthyl-, diphenylmethane and diphenylether radicals are particularly preferred. z represents an integer of from 1 to 4, especially 2 or 3. Inventive compounds produced by using iso(thio)cyanates in which $R^3$ represents an optionally substituted aliphatic radical containing 1 – 20 carbon atoms, preferably 2 to 6 carbon atoms, a cycloaliphatic radical containing 5 to 12 carbon atoms and an aromatic or cycloaliphatic heterocyclic radical which contains or is substituted by hetero atoms such as N, O or S and has 5 to 12 ring atoms have not yet been obtainable.

The monisocyanates used for this invention are aliphatic and aromatic compounds which contain one NCO group in the molecule and which may optionally be substituted by hetero atoms, for example alkylisocyanates such as ethyl-, methyl-, butyl-, dodecyl-, stearyl-, isopropyl-, or nonylisocyanate, aromatic, optionally substituted monoisocyanates such as phenyl-, tolyl-isocyanate, isopropyl-, nonyl-, nitro-, alkoxy-, aroxy-, chloro-, dichloro-, trichloro-, tetrachloro-, pentachloro-, benzyl- or bromophenyl isocyanate or isocyanatobenzoic acid esters, isocyanatophthalic acid esters and isocyanato-isophthalic acid esters, isocyanatobenzonitrile, cycloaliphatic isocyanates such as cyclohexyl isocyanate and unsaturated isocyanates such as allyl, oleyl or cyclohexenyl isocyanate.

The starting components used according to the invention may also be aliphatic, cycloaliphatic, araliphatic, aromatic and heterocyclic polyisocyanates (see Annalen, 562, pages 75 to 136), for example ethylene diisocyanate, tetramethylene-1,4-diisocyanate, hexamethyl-1,6-diisocyanate, dodecane-1,12-diisocyanate, cyclobutane-1,3-diisocyanate, cyclohexane-1,3-and -1,4-diisocyanate and any mixtures of these isomers, 1-isocyanato-3,3,5-trimethyl-5-isocyanatomethyl-cyclohexane (U.S. Pat. No. 3,401,190), hexahydrotolylene-2,4- and -2,6-diisocyanate and any mixtures of these isomers, hexahydro-1,3- and/or -1,4-phenylene diisocyanate, perhydrodiphenylmethane-2,4'- and/or 4,4'-diisocyanate, phenylene-1,3- and -1,4-diisocyanate, tolylene-2,4- and -2,6-diisocyanate and any mixtures of these isomers, diphenylmethane-2,4'- and/or 4,4'-diisocyanate, naphthylene-1,5-diisocyanate, triphenyl methane-4,4',-4''-triisocyanate, polyphenyl-polymethylene polyisocyanates which can be obtained by aniline-formaldehyde condensation followed by phosgenation and which have been described e.g. in British Patent Specification Nos. 874,430 and 848,671, perchlorinated arylpolyisocyanates such as those described e.g. in U.S. Pat. No. 3,277,138, polyisocyanates which contain carbodiimide groups as described in U.S. Pat. No. 3,152,162, the diisocyanates described in U.S. Pat. Specification No. 3,492,330, polyisocyanates which contain allophanate groups as described e.g. in British Pat. Specifications Nos. 994,890 and 1,288,688 and U.S. Pat. No. 3,769,318, polyisocyanates which contain isocyanurate groups as described e.g. in British Pat. Specifications Nos. 843,841, 1,091,949, 1,267,011, 1,304,936 and 1,305,036, polyisocyanates which contain urethane groups as described e.g. in British Pat. Specification 1,303,201 or in U.S. Pat. No. 3,394,164, polyisocyanates which contain acylated urea groups according to U.S. Pat. No. 3,517,039, polyisocyanates which contain biuret groups as described e.g. in U.S. Pat. Specification No. 3,124,605, in British Pat. Specifications Nos. 889,050 and 1,308,652, polyisocyanates prepared by telomerisation reactions as described e.g. in U.S. Pat. Specification 3,654,106, polyisocyanates which contain ester groups as mentioned e.g. in British Pat. Specifications Nos. 956,474, 1,072,956 and 1,086,404 and in U.S. Pat. Specification 3,567,763 and reaction products of the above mentioned isocyanates with acetales in accordance with U.S. Pat. Specification 3,120,502.

The distillation residues obtained from the commercial production of isocyanates and still containing isocyanate groups may also be used, optionally dissolved in one or more of the above mentioned polyisocyanates. Any mixtures of the above mentioned polyisocyanates may also be used.

It is preferred to use commercially readily available mixtures of tolylene diisocyanates, m-phenylenediisocyanate, any phosgenated condensates of aniline and formaldehyde which have a polyphenylene-methylene structure and the symmetric compounds 4,4'-diisocyanatodiphenylmethane, 4,4'-diisocyanatodiphenylether, p-phenylene diisocyanate, 4,4'-diisocyanatodiphenyl-dimethylmethane, analogous hydroaromatic diisocyanates and hexamethylene diisocyanate.

The isocyanates may be used in their free form or partly or completely in the form of masked isocyanates which react as the corresponding free isocyanates under the given reaction conditions and have been obtained by reaction with compounds which contain reactive hydrogen atoms.

The masked isocyanate compounds used are preferably carbamic acid esters obtained from aromatic and aliphatic mono- and polyhydroxy compounds, e.g. carbamic acid esters of the general formulae $$\left[ R^3(-NH-\underset{\underset{O}{\|}}{C}-O-A)_z \text{ and } -\underset{\underset{O}{\|}}{C}-NH-R^3-NH-\underset{\underset{O}{\|}}{C}-O-B-O- \right]$$

in which $R^3$ denotes the organic radical of an iso(thio)cyanate and has the meaning given above and A, which represents the organic radical of a monohydroxy compound, and B, which represents the organic radical of a difunctional or trifunctional hydroxy compound, may stand for an aliphatic radical containing 1 – 10 carbon atoms, a cycloaliphatic radical containing 5 – 10 carbon atoms, an aliphatic-aromatic radical containing 6 – 12 carbon atoms and an romatic radical containing 5 – 12 carbon atoms, all of which radicals may also be substituted; z represents an integer of from 1 to 4, preferably 2 to 3.

Examples include the carbamic acid esters of phenol, isomeric cresols and commercial mixtures thereof and similar aromatic hydroxyl compounds, aliphatic monoalcohols such as methanol, ethanol, propanol, isopropanol, butanol, isobutanol, cyclohexanol, benzyl alcohols and aliphatic diols or polyols such as ethylene glycol and trimethylolpropane.

The O-alkylurethanes may be introduced into the reaction mixture as such or produced in situ by reaction of polyiso(thio)cyanates with alcohols. If O-alkylurethanes are used for the reaction, up to 100 % of the isocyanate groups may be present in the O-alkylurethane form.

Instead of the above mentioned (poly)isocyanates, the analogous (poly)isothiocyanates may be used.

Particularly suitable α-halocarboxylic acid amides for the process are those which are derived from aliphatic α-halocarboxylic acids of the formula

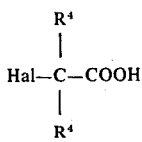

and their derivatives. In the above formula, Hal denotes halogen, e.g. F, Cl, Br or I, preferably Cl; the two groups $R^4$ may be the same or different and denotes an aromatic radical containing 5 – 10 carbon atoms which may also be substituted, an aliphatic radical containing 1 – 20 carbon atoms, a cycloaliphatic radical containing 5 – 10 carbon atoms or hydrogen. Two radicals $R^4$ together with the $\alpha$-carbon atoms may form a cycloaliphatic ring containing 5 to 7 ring members. The derivatives of these acids are preferably the acid halides (acid chlorides; the $C_1$-$C_{10}$ alkyl esters (methyl-,ethyl-,isopropyl- or hexylesters) and the $C_6$ - $C_{10}$ aryl esters (phenyl-, cresyl- and naphthylesters).

Preferred examples of $\alpha$-halocarboxylic acids and their derivatives are chloroacetic acid, and $\alpha$-halogenated, e.g. $\alpha$-chlorinated or $\alpha$-brominated propionic, butyric, 2-ethylhexanoic, stearic, phenylacetic, diphenylacetic, dimethylacetic, isopropylacetic and cyclohexanoic acid.

Compounds which contain several $\alpha$-halocarboxylic acid groups are represented by the following formula

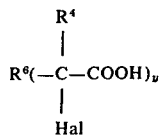

are also suitable. In the above formula, $R^6$ denotes an aliphatic radical containing 1 – 10 carbon atoms, a cycloaliphatic radical containing 5 – 10 carbon atoms, an aliphatic aromatic radical containing 6 – 10 carbon atoms, an aromatic radical containing 5 – 10 carbon atoms or a single bond and $y$ represents an integer of from 1 to 3, preferably 2 to 3. These compounds are formed, for example, by $\alpha,\alpha'$-chlorination or -bromination of polybasic carboxylic acids such as succinic, adipic, glutaric, sebacic or phenylene diacetic acid.

The various stereoisomeric forms of dichloro- and dibromo-succinic acids which can be obtained from maleic and fumaric acid are preferred.

Suitable monoamines and polyamines for preparing the halocarboxylic acid amides are compounds of the formula $$R^5(-NH_2)_x \qquad \text{IX}$$

in which $R^5$ denotes optionally substituted aliphatic, aromatic, aliphaticarmatic or heterocyclic radicals. $R^5$ preferably has the same meaning as $R^3$. $x$ denotes an integer of from 1 to 4, preferably 2 to 3. The preferred amines used are propylamine, cyclohexylamine, aniline, hexamethylene diamine, m- and p-phenylene diamine, 4,4'-diaminodiphenylmethane, 4,4'-diaminodiphenylether, tolylene-2,4- or -2,6-diamine and the commercial amine mixture obtained by condensation of aniline with formaldehyde.

Mono- and poly-functional $\alpha$-halocarboxylic acid amides represented by the general formula

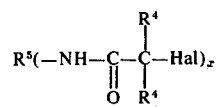

in which $R^4$, $R^5$, Hal and $x$ have the meanings indicated above may be obtained in known manner, e.g. from $\alpha$-halocarboxylic acid halide derivatives or $\alpha$-halocarboxylic acid ester derivatives of compound VIII and amines of formula IX or from the isocyanates (X) corresponding to these amines and $\alpha$-halocarboxylic acids (VIII).

Monofunctional and polyfunctional $\alpha$-halocarboxylic acid amides represented by the formula

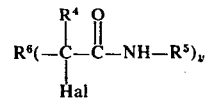

in which $R^4$, $R^5$, $R^6$, Hal and $y$ have the meanings already indicated may similarly be obtained from the corresponding derivatives of compound XI and amines of formula IX, preferably with $x = 1$ (or more) or the corresponding isocyanates (X).

To carry out the process according to the invention, the starting materials may be dissolved in a solvent and then heated to temperatures of about 60° – 350°C. A slow stream of inert gas (e.g. nitrogen or $CO_2$) is advantageously passed over or through the reacting solution to remove the hydrogen halide evolved more quickly. The reaction is generally finished when evolution of the hydrogen halide ceases. The reaction last usually from 1 to 50 hours, preferably 1 – 20 hours.

The reaction may be modified by slowly adding one or both reactants to the inert solvent or to the other reactant, optionally in solution only at elevated temperatures, for example at 80° to 220°C.

On the other hand it is not necessary to prepare the $\alpha$-halocarboxylic acid amides separately and isolated before they are used for the process of preparing the inventive polyhydantoins. They may also be prepared by a one pot reaction, optionally in a solvent, for example by reacting the corresponding $\alpha$-halocarboxylic acids with an equivalent quantity of the isocyanate which corresponds to the amine component or by reacting the corresponding $\alpha$-halocarboxylic acid halides, or the esters obtained from them by a reaction with phenolic reactants such as monoalcohols or polyols, with the amine component, e.g. at temperatures of between −20° and 200°C, and they may then be reacted directly, for example within the same temperature range, with the same or another of the above mentioned isocyanate components to produce the compounds which contain hydantoin rings.

Alternatively, the reaction may be carried out stepwise by first reacting part of the isocyanate or O-alkylurethane with the α-halocarboxylic acid amide derivative, e.g. at 50° to 200°C, and then reacting the product with the same or another of the above mentioned isocyanate components, O-phenylurethanes or O-alkylurethanes, for example at the same temperature range.

Solvents which are inert in the reaction and towards the reaction products may be used, for example higher boiling, optionally halogenated aliphatic and aromatic hydrocarbon solvents such as paraffin oils, chloroparaffin, chlorobenzene, dichlorobenzene, nitrobenzene, tetralin, decalin, alkylbenzenes or alkylnaphthalenes and diphenylethers.

It is preferred, however, to use solvents which react with the isocyanates to form so-called masked isocyanates as already described above. These solvents may if desired be used together with the solvents mentioned above. Solvents which form masked isocyanates are in particular solvents which contain active hydrogen atoms which react with the isocyanates to form isocyanate derivatives such as urethanes which are easily reconverted into the isocyanates by heat. Phenolic solvents are particularly preferred, e.g. phenol, cresols or mixtures thereof.

According to the invention, the reaction may be accelerated by catalysts. The following are examples of suitable catalysts:

(1) Tertiary amines, such as triethylamine, tributylamine, N-methylmorpholine, N-ethylmorpholine, N-cocomorpholine, N,N,N',N'-tetramethyl-ethylenediamine, 1,4-diaza-bicyclo(2,2,2)-octane, N-methyl-N'-dimethylaminoethyl-piperazine, N,N-dimethylbenzylamine, bis-(N,N-diethylaminoethyl)-adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimidazole and 2-methylimidazole.(2) Tertiary amines containing hydrogen atoms which are reactive with isocyanate groups, e.g. triethanolamine, triisopropanolamine, N-methyl-diethanolamine, N-ethyl-diethanolamine, N,N-dimethyl-ethanolamine and their reaction products with alkylene oxides such as propylene oxide and/or ethylene oxide;

(3) Silaamines which contain carbon-silicon bonds (see German Patent Specification No. 1,229,290), e.g. 2,2,4-trimethyl-2-silamorpholine and 1,3-diethylaminomethyl-tetramethyl-disiloxane;

(4) Bases which contain nitrogen, such as tetraalkylamomnium hydroxides and hexahydrotriazines;

(5) Organic metal compounds, in particular iron, lead and/or tin. The organic tin compounds used are preferably tin(II) salts of carboxylic acids such as tin(II) acetate, tin(II) octoate, tin(II) ethylhexoate and tin(II) laurate and dialkyl tin(IV) salts such as dibutyl tin dichloride, acetate, laurate or maleate or dioctyl tin diacetate, or iron salts such as iron acetylacetonate or iron chloride, lead oxide, lead carbonate or lead carboxylate.

Other catalysts which may be used in the process according to the invention have been described in Kunststoff-Handbuch, Volume VII, published by Vieweg and Hochtlen, Carl-Hanser-Verlag, Munich 1966, on pages 96 to 102, and in High Polymers, Vol. XVI, Part I, (Polyurethanes-Chemistry), published by Saunders and Frisch, Interscience Publishers, New York 1962, on pages 129 – 217.

The compounds obtained according to the invention may be high molecular or low molecular weight compounds. This depends mainly on the choice of starting materials and the molar ratios in which they are used. 1) When "monovalent" reactants are used, compounds with only one hydantoin ring are obtained. 2) If 1 mol of a bis-α-halocarboxylic acid amide is reacted with 2/n mol of a polyiso(thio)cyanate which contains n NCO groups, then a high molecular weight product is obtained if n > 1, preferably n = 2, for example when a diisocyanate of formula II is reacted with a bis-α-halocarboxylic acid amide of formula IV, then a high molecular weight product which contains the following recurrent structural unit is obtained:

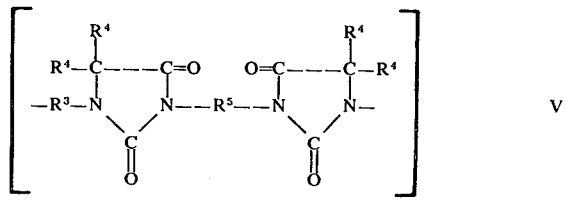

V (3) If, on the other hand, one mol of a bis-α-halocarboxylic acid amide is reacted with 4/n mol of a polyiso(thio)cyanate which contains n NCO groups per molecule, then if n > 1, preferably n = 2, the product obtained contains n hydantoin rings per molecule, for example when an isocyanate of formula II is reacted with a bis-α-halocarboxylic acid amide of the formula IV, then a hydantoin ring which contains NCO groups as represented by the following formula is obtained:

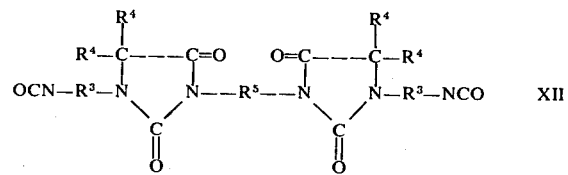

XII

If the reaction is carried out with a derivative of a diisocyanate, i.e. a so-called masked diisocyanate, or if a phenolic solvent is used, e.g. phenol, cresols or mixtures thereof, then products of the following formula are obtained:

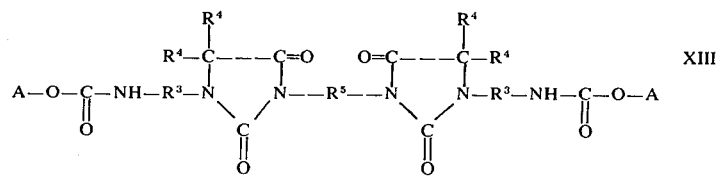

XIII in which A denotes an aliphatic or aromatic radical as described above. 4) If for 1 mol of bis-α-halocarboxylic acid amide there are used between 2/n and 4/n mol of a polyiso(thio)cyanate which contains n NCO groups per molecule, then if n > 1, preferably n = 2, products of the following formula are obtained:

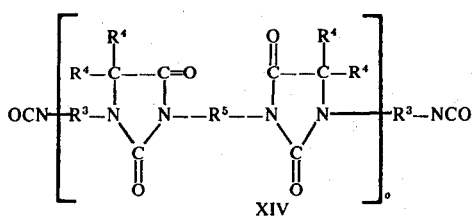

XIV in which o = 2 to about 200, especially 2 – 50, and if masked isocyanates or phenolic solvents are used, then products of the following formula are obtained in analogous manner:

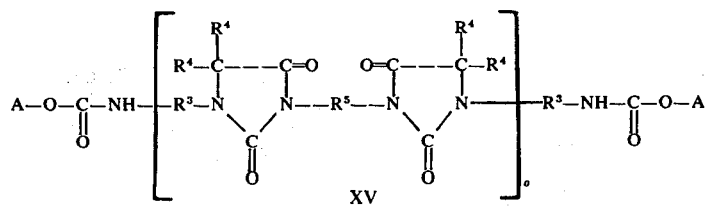

XV (5) If in accordance with 2–4α,α'-dihalodicarboxylic acid diamides of formula VI or of formula XXI for y = 2 are used instead of bis-α-halocarboxylic acid amides in analogous form, then the reaction products obtained are dimeric to polymeric products in which the hydantoin rings are also linked through the carbon atoms in the 5,5'-position.

These reaction products are specifically characterised as follows:

a. Instead of high molecular weight products of Formula V, products with recurrent structural units of the following formula are obtained:

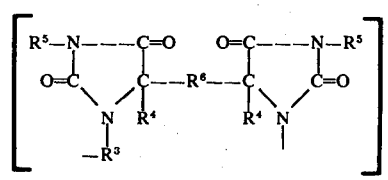

VII b. instead of hydantoins of the formula XII which contain NCO groups, hydantoins of the following formula are obtained:

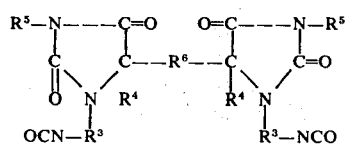

XVI or in the masked form

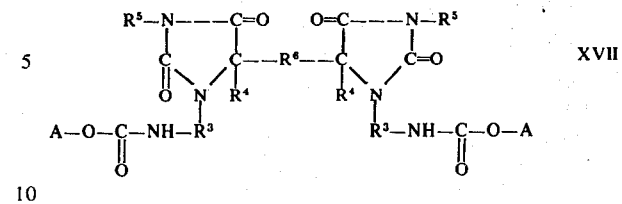

XVII c. instead of oligomers of formula XIV, oligomers of the following formula are obtained:

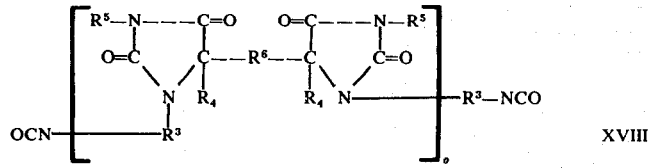

XVIII or in the masked form:

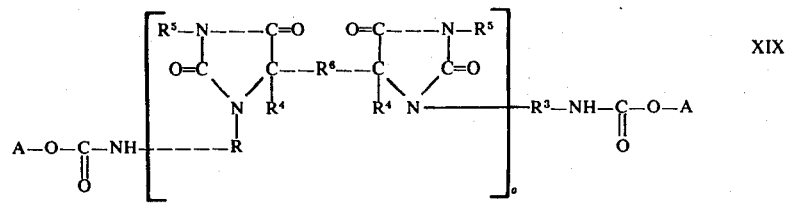

XIX

Since the inventive reaction is generally carried out in solvents, the products are also obtained as solutions. These solutions may be used directly as coating materials. When heated to elevated temperatures the products of the invention are converted into hard, non-fusible products. Thus when heated to temperatures of about 100° to 500°C, they give rise to temperature resistant coatings which have extremely high chemical, thermal and physical resistance. It is, therefore, possible to obtain coatings exhibiting outstanding flexibility, surfacehardness, abrasion resistance and resistance to all the conventional solvents such as alcohols, aromatic and aliphatic hydrocarbons, esters, ethers and ketones, and even to water, by applying solutions of the inventive products to heat-resistant supporting bases comprising for example, metals, ceramics, glass or asbestos fibres, or fabrics made from such fibres, or even to other adequately temperature-resistant synthetics, and then stoving at elevated temperatures.

The iso(thio)cyanate groups still present in the products would be expected to form high molecular weight materials by chain lengthening or cross-linking reactions although cross-linked substances may also be obtained from isocyanates which are more than divalent or from α-halocarboxylic acid amides (XX) of more than divalent amines or from the amides (XX) of polyfunctional α-halocarboxylic acids of formula XI already mentioned above, in which the proportion of cross-linking component may vary within wide limits. Thus, for example, an oligomer which consists of three hydantoin rings and three optionally masked NCO groups is formed from 1 mol of 4,4',4''-trichloroacetanilidomethane and 3 mols of 4,4'-diisocyanato-diphenylmethane. In stoichiometric reaction mixtures according to equation 2, the cross-linking component may advantageously consist of a more than difunctional iso(thio)cyanate and/or a more than difunctional α-halocarboxylic acid amide derivative, and the proportion of NCO groups or α-halocarboxylic acid amide groups present in these components may be 0.2 to 50 mols %, preferably 0.5 to 10 mols %. The synthetic resins, coatings and sheets obtained in this way have excellent flexibility and surface hardness as well as excellent abrasion resistance and resistance to all the usual solvents such as alcohols, aromatic and aliphatic hydrocarbons and esters, ethers and ketones as well as water.

The outstanding properties of the inventive products which guarantee synthetic resins, coatings or structures of excellent flexibility, surface-hardness and high temperature resistance, remain largely unaffected, or can be varied as required, when other polymers known per se are jointly used, for example, polyesters, polyamides, polyurethanes, polyolefins, polyacetals, polyepoxides, polyimides, polyamide-imides, polyimino-polyesters and polyimide isocyanates. The quantities in which these polymers are used will largely depend upon the properties required of the end product and the weight ratio of the polymers of the invention to the known polymers may conveniently vary from 10 : 90 to 90 : 10. They are preferably mixed in a weight ratio of 30 : 70 to 70 : 30. These known polymers may be added to the polyhydantoins or may even be incorporated in them by polymerisation and condensation.

There should also be particularly mentioned the modification which is obtained by adding polyesters which contain reactive hydroxyl groups. When these polyesters are used with high or low molecular weight compounds according to this invention which contain masked or free NCO groups as for instance described in the formulae VIII - XI they cause chain lengthening or cross-linking of the molecules by way of urethane groups, either directly or after removal of the masking group. Coatings obtained from these polymers have also an excellent flexibility and surface-hardness and are high temperature resistant.

Suitable polyesters containing hydroxyl groups include the known types which can be obtained by routine methods from polycarboxylic acids, for example succinic acid, adipic acid, sebacic acid, phthalic acid, isophthalic acid, terephthalic acid or maleic acid and polyalcohols, for example glycol, diethylene glycol, triethylene glycol, propylene glycol, dipropylene glycol, glycerol, 1,1,1-tri-methylol propane or pentaerythritol.

EXAMPLE 1 a. A solution of 56 g NaOH in 140 g of water and 113.0 g of chloroacetyl chloride are added alternately to 74.4 g of aniline in a mixture of 200 g of tetrahydrofuran and 100 g of water, and the reaction mixture is then stirred for 30 minutes at room temperature. The product is worked up by evaporating the organic solvent under vacuum and recrystallising the resulting precipitate. Yield: 108 g (87% of the theory) of α-chloroacetanilide (alcohol), m.p.: 133°C.

Other α-halocarboxylic acid amides may be prepared in a manner analogous to Example 1 a), for example:

1,6-Bis-α-chloroacetamido-hexane, m.p.: 128°–130°C (methanol);

1,3-Bis-α-chloroacetamido benzene m.p.: 220°–221°C (DMF/acetonitrile);

4,4'-bis-α-chloroacetamido-diphenylmethane, m.p.: 232°C (DMF/alcohol);

4,4'-bis-α-chloroacetamido-diphenylether, m.p.: 234°–235°C (dioxane).

b. 120 g of m-cresol are added to 31.2 g of α-chloroacetanilide, and 25.0 g of 4,4'-diisocyanatodiphenylmethane are then introduced at 80°C at a rate adjusted to the exothermic reaction. The reaction mixture is slowly heated to 185°C and kept at this temperature for about 12 hours, or until evolution of HCl ceases, anhydrous nitrogen being passed through at the same time.

29 g (56% of the theory) of a dihydantoin of the following structure

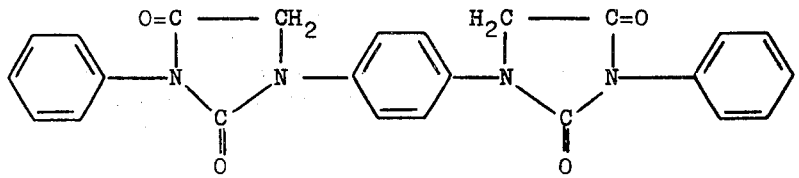

are obtained after precipitation with alcohol and recrystallisation from glycol monomethylether. The hydrantoin ring structure of this product is confirmed by the typical IR absorption at 1700 cm$^{-1}$, and 1755 cm$^{-1}$, nitrogen content is 10.3% and the melting point is 208°–210°C. c. Hydantoin (1 b) is also obtained from the following reaction:

19.0 g of chloroacetic acid and 23.8 g of phenylisocyanate are first mixed with 120 g of m-cresol at 80°C. The reaction mixture is then slowly heated to 150°–160°C and finally, after evolution of $CO_2$ has ceased, 25.0 g of 4,4'-diisocyanatodiphenylmethane are added at 120°C and the reaction mixture is then heated to 185°C. The reaction mixture is then kept at this temperature while anhydrous nitrogen is passed through the mixture for about 12 hours or until evolution of HCl ceases. Precipitation with alcohol yields a dihydantoin which has the typical IR absorption band at 1700 and 1755 cm$^{-1}$, a nitrogen content of 10.0%, a chlorine content below 0.2% and a melting point of 192° – 195°C.

EXAMPLE 2

52.2 g of 1,3-bis-α-chloroacetamido-benzene in 160 g of m-cresol are mixed with 32.6 g of 1,3-diisocyanato-benzene at 80°C at a rate adjusted to the exothermic reaction. The reaction mixture is then heated to about 185°C and kept at this temperature while anhydrous nitrogen is passed through for about 12 hours until evolution of HCl ceases. 230 g of an approximately 30% solution of polyhydantoin in m-cresol are obtained. The solution has the viscosity of 7680 cP$_{20°}$ $_c$ and a chlorine content below 0.3%. The presence of the hydantoin ring structure is confirmed by the typical IR absorption band at 1700 and 1755 cm$^{-1}$.

EXAMPLE 3

200 g of the solution obtained according to Example 2 are mixed with 3000 g of methanol (or acetone) with vigorous stirring, and the precipitate formed is washed with methanol and dried at 80°C under vacuum.

130 g of the polyhydantoin described in Example 2 are obtained. It has a softening point of 300°C, shows the typical IR absorption bands at 1700 and 1755 cm$^{-1}$ and has a nitrogen content of 15.9%.

EXAMPLE 4

53.8 g of 1,6-bis-α-chloroacetamido-hexane in 170 g of m-cresol are reacted by the method described in Example 2 with 33.6 g of 1,6-diisocyanatohexane, first at 80°C and then for about 12 hours at 185°C until evolution of HCl ceases. About 242 g of an approximately 30% cresolic polyhydantoin solution with a chlorine content below 0.2%, a viscosity of 12 350 cP$_{20°}$ $_c$ and the typical hydantoin absorption bands at 1700 and 1755 cm$^{-1}$ remain behind.

The polyhydantoin can be precipitated from its solution with acetone in accordance with the method given in Example 3. 100 g of polyhydantoin containing 0.25% of chlorine and 15.2% of nitrogen are obtained after suction filtration and drying.

EXAMPLE 5

50.0 g of 4,4'-diisocyanatodiphenylmethane are added to 52.2 g of 1,3-bis-α-chloroacetamido-benzene and a mixture of 110 g of m-cresol and 100 g of phenol at 120°C at a rate adjusted to the exothermic rise in temperature and the reaction mixture is then heated to 185°C and kept at this temperature for about 12 hours while nitrogen is passed through it.

297 g of an approximately 30% solution of polyhydantoin which has a chlorine content below 0.2% and a viscosity of 9600 cP$_{20°}$ $_c$ and shows the typical hydantoin IR absorption bands at 1700 and 1755 cm$^{-1}$ are obtained.

Precipitation from methanol carried out in accordance with Example 3 yields a solid polyhydantoin containing 12.5% of nitrogen.

EXAMPLE 6

A solution of 50.0 g of 4,4'-diisocyanatodiphenylmethane in 150 g of toluene is added to 52.2 g of 1,3-bis-α-chloroacetamido-benzene in 210 g of m-cresol at 80°C at a rate adjusted to the exothermic reaction. The reaction mixture is then slowly heated to 180°C, whereby the toluene is split off, and it is then kept at 190°C for about 10 hours.

The resulting approximately 30% solution of polyhydantoin in cresol shows the characteristic IR absorption bands at 1700 and 1755 cm$^{-1}$ for the hydantoin ring and has a viscosity of 7283 cP$_{20°}$ $_c$.

EXAMPLE 7

210 g of m-cresol are mixed with 34.8 g of tolylene diisocyanate (isomeric mixture: 2,4 : 2,6 = 80 : 20) and 70.2 g of 4,4'-bis-α-chloroacetamido-diphenylmethane are then added at 120°C and the reaction mixture is immediately heated to 185°C while nitrogen is passed through it.

After a reaction time of about 15 hours at a temperature of 185° – 200°C, about 300 g of a cresol polyhydantoin solution are left behind. This solution has a viscosity of 6470 cP$_{20°}$ $_c$ and a chlorine content below 0.2% and shows the IR absorption bands at 1700 and 1755 cm$^{-1}$.

EXAMPLE 8

50.0 g of 4,4'-diisocyanatodiphenylmethane followed by 70.2 g of 4,4'-bis-α-chloroacetamidodiphenylmethane are added in the course of about one hour to 250 g of m-cresol at 120°C, the rate of addition being adjusted to the heat evolved in the exothermic reaction. The reaction mixture is then directly heated to about 185°C and kept at this temperature for about 12 hours, until evolution of HCl ceases, and anhydrous nitrogen is passed through at the same time.

Approximately 355 g of an approximately 30% polyhydantoin solution in cresol which has a viscosity of 12 770 cP$_{20°}$ $_c$ and a chlorine content below 0.2% are obtained. The solution shows the typical hydantoin absorption bands at 1700 and 1755 cm$^{-1}$.

The cresolic solution is precipitated by mixing it with 5000 g of methanol with stirring. After suction filtration and drying, 240 g of a polyhydantoin which contains 10.5% of N and less then 0.2% of Cl remain behind.

EXAMPLE 9

Using the method described in Example 8, 240 g of m-cresol are mixed with 50.4 g of 4,4'-diisocyanatodiphenyl ether followed by 70.6 g of 4,4'-bis-α-chloroacetamidodiphenylether at 120°C and the mixture is then reacted at 185°C for 14 hours. 346 g of an approximately 30% polyhydantoin solution which has a chlorine content below 0.2% and a viscosity of 12460 cP$_{20°}$ $_c$ are obtained. Precipitation of this solution in methanol yields 210 g of a polyhydantoin with a nitrogen content of 10.4% and a chlorine content below 0.2%. The hydantoin structure is in both cases confirmed by the IR absorption bands at 1700 and 1755 cm$^{-1}$.

EXAMPLES 10 – 13

Using the methods described in Example 8, 250 g (Examples 10 and 11) or 255 g (Example 12) or 260 g (Example 13) of m-cresol are mixed with 50.0 g (Example 10) or 51.0 g (Example 11) or 53.0 g (Example 12) or 55.0 g (Example 13) of 4,4'-diisocyanatodiphenylmethane followed by 70.6 g of 4,4'-bis-α-chloroacetamidodiphenylether at 120°C and the reaction mixture is then kept at 185°C for about 20 hours, until evolution of HCl ceases. The resulting solutions all contain less than 0.2% of chlorine and show the typical hydantoin bands at 1700 and 1755 cm$^{-1}$ in the IR spectrum.

Example 10 yields 356 g of a polyhydantoin solution with a viscosity of 11 209 cP$_{20°}$ $_c$; Example 11: 357 g of polyhydantoin solution, viscosity 14 117 cP$_{20°}$ $_c$; Example 12: 364 g of polyhydantoin solution, viscosity 25,378 cP$_{20°}$ $_c$; Example 13: 371 g of polyhydantoin solution, viscosity 12,835 cP$_{20°}$ $_c$.

EXAMPLE 14

51.0 g of 4,4'-diisocyanatodiphenylmethane are added to 220 g of m-cresol in the course of 1 hour at 120°C. The reaction mixture is then heated to 185°C, 52.2 1 of 1,3-bis-α-chloroacetamidobenzene are introduced and the mixture is kept at 185° – 190°C for about 12 hours, until evolution of HCl ceases, and anhydrous nitrogen is passed through at the same time.

About 308 g of an approximately 30% polyhydantoin solution in cresol with a viscosity of 30 843 $cP_{20°C}$ and a chlorine content below 0.2% are obtained. In the IR spectrum, the solution shows the typical hydantoin absorption band at 1700 to 1755 $cm^{-1}$.

EXAMPLE 15

99.1 g of 4,4'-diaminodiphenylmethane followed by 113.0 g of chloroacetylchloride are added to 620 g of m-cresol. The reaction mixture is then kept at 150°C until evolution of HCl ceases and at the same time anhydrous nitrogen is passed through it. 125.1 g of 4,4'-diisocyanatodiphenylmethane are then added at 120°C and the reaction mixture is immediately heated to 190°C. After 15 hours at 190°C, 884 g of a polyhydantoin solution in cresol with a chlorine content below 0.2% and a viscosity of 8370 $cP_{20°C}$ are left. The solution shows the typical hydantoin absorption bands at 1700 and 1755 $cm^{-1}$.

EXAMPLE 16

32.0 g of 1,3-diisocyanatobenzene followed by 37.8 g of chloroacetic acid are added to 210 g of m-cresol at 120°C at a rate adjusted to the exothermic reaction. The reaction mixture is heated to 150° – 160°C at a rate adjusted to the evolution of $CO_2$. When evolution of $CO_2$ ceases, 51.0 g of 4,4'-diisocyanatodiphenylmethane are introduced at 120°C and the reaction mixture is then immediately heated to 185°C and kept at this temperature for about 12 hours, until evolution of HCl ceases, while anhydrous nitrogen is passed through.

298 g of an approximately 30% polyhydantoin solution in cresol with a viscosity of 20 700 $cP_{20°C}$ and a chlorine content below 0.2% are obtained. The existence of the hydantoin ring structure is confirmed by the typical IR absorption bands at 1700 to 1755 $cm^{-1}$. The polyhydantoin precipitated as described in Example 3 contains 14.3% of nitrogen.

EXAMPLE 17 a) 53.0 g of 4,4'-diisocyanatodiphenylmethane are added to 220 g of m-cresol at 120°C. 1.12 g of dibromosuccinic acid and 52.2 g of 1,3-bis-α-chloroacetamidobenzene are then added at a rate adjusted to the exothermic reaction. The mixture is slowly heated to 185° – 190°C and kept at this temperature until evolution of HCl ceases, anhydrous nitrogen being passed through it at the same time. After about 15 hours, 310 g of a solution in cresol of a slightly branched polyhydantoin are obtained. The solution shows the characteristic IR absorption bands at 1700 to 1755 $cm^{-1}$ and has a chlorine content below 0.2% and a viscosity of 13,538 $cP_{20°C}$.

b) 52.5 g of 4,4'-diisocyanatodiphenylmethane followed by 2.58 g of 4,4'-bis-(4-anilido-2,3-dibromosuccinic acid-amido)-diphenylmethane and 52.2 g of 1,3-bis-α-chloroacetamidobenzene are added to 220 g of m-cresol at 120°C. The reaction mixture is immediately heated to 185° – 190°C and the reaction is completed by the method described in Example 17 a.) 312 g of the cresolic solution of a slightly branched polyhydantoin which shows the typical IR absorption bands at 1700 and 1755 $cm^{-1}$ are obtained. The solution has a viscosity of 16 820 $cP_{20°C}$ and a chlorine content below 0.2%.

EXAMPLES 18 – 22

210 g m-cresol are mixed with the catalysts indicated below. 51.0 g of 4,4'-diisocyanatodiphenylmethane followed by 52.2 g of 1,3-bis-α-chloroacetamidobenzene are then added at 120°C and the reaction mixture is then heated to 185°C for about 12 hours while anhydrous nitrogen is passed through it.

The calculated quantity of cresolic solution of a polyhydantoin with the typical IR absorption bands at 1700 and 1755 $cm^{-1}$ is obtained in all cases. The solutions have approximately the viscosities indicated below. Their chlorine content is in all cases below 0.2%.

EXAMPLE 18

0.009 g of triethylenediamine Viscosity: 12 110 $cP_{20°C}$

EXAMPLE 19

0.041 g of iron acetylacetonate—Viscosity: 12 586 $cP_{20°C}$

EXAMPLE 20

0.047 g of dibutyl tin dilaurate—Viscosity: 11 261 $cP_{20°C}$

EXAMPLE 21

0.039 g of tin(II) octoate—Viscosity: 10 490 $cP_{20°C}$

EXAMPLE 22

0.010 g of PbO—Viscosity: 9 720 $cP_{20°C}$

EXAMPLE 23

50.0 g of 4,4'-diisocyanatodiphenylmethane followed by 35.3 g of 4,4'-bis-α-chloroacetamidodiphenylether are added to 180 g of m-cresol at 120°C in the course of one hour at a rate adjusted to the exothermic reaction, and the reaction mixture is then kept at about 185°C for about 15 hours, until evolution of HCl ceases, and anhydrous nitrogen is passed through the reaction mixture at the same time.

258 g of a solution of a dihydantoin in cresol is obtained. The solution has a concentration of approximately 30%, based on the free isocyanate. The dihydantoin has the following structure (analogous to formula XIII)

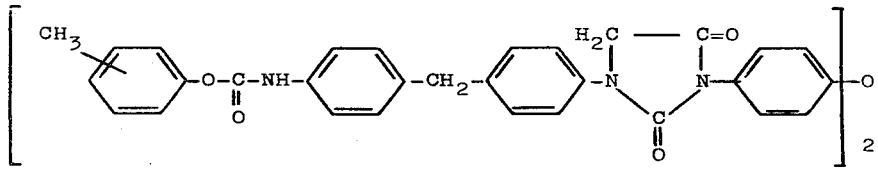

The hydantoin ring structure is confirmed by the typical IR absorption band at 1700 and 1755 $cm^{-1}$. The viscosity of the solution is 6340 $cP_{20°C}$ and its chlorine content is below 0.2%. The hydantoin-isocyanate derivative precipitated by the method of Example 3 contains 8.1 % of nitrogen.

200 g of an approximately 30 % solution of the dihydantoin in cresol is mixed with a solution of 350 g of a polyester obtained from 1,6 mol terephthalic acid dimethylester, 1,2 mol ethylene glycol and 0,8 mol glycerine in 820 g m-cresol at 50°C. A homogeneous solution having a viscosity of 7480 $cP_{20°C}$ is obtained. This solution is applied to metal sheet and stoved to a clear, hard lacquer film in stages at 240°C and 300°C.

EXAMPLE 24

160 of m-cresol are mixed with 37.5 g of 4,4'-diisocyanatodiphenylmethane and 35.3 g of 4,4'-bis-α-chloroacetamido-diphenylether at 120°C in accordance with the methods described in Example 23 and then kept at 185°C for 12 hours.

225 g of a cresolic oligohydantoin solution which has a concentration of about 30% with respect to the free isocyanate content is obtained. The hydantoin structure in the solution is demonstrated by the IR absorption at 1700 and 1755 $cm^{-1}$. The viscosity of the solution is 11 810 $cP_{20°C}$ and the chlorine content is below 0.2%. When the polyhydantoin solution is titrated to determine the amount of masked isocyanate, it is found that it still contains 1.4% of available NCO groups.

200 g of the above obtained 30 % solution of an oligohydantoin in cresol is mixed with a solution of 200 g of a polyester obtained from 1,6 mol terephthalic acid dimethylester, 1,2 mol ethylene glycol and 0,8 mol glycerine and having 6 % by weight OH groups in 480 g m-cresol at 50°C. A homogeneous solution having a viscosity of 5800 $cP_{20°C}$ is obtained. This solution is applied to a warm metal sheet and stoved for half an hour at 230°C and about 3 minutes at 300°C to a clear lacquer film having a pencil hardness of 5 H.

EXAMPLE 25

52.2 g of 1,3-bis-α-chloroacetamidobenzene are added to a solution of 52.2 g of tolylene diisocyanate (mixture of isomers 2,4 : 2,6 = 80 : 20) in 150 g of toluene at 100°C. The mixture is slowly heated to 180°C, the toluene being thereby evaporated, and the mixture is then kept at 185°C for about 20 hours while nitrogen is passed through it. Approximately 90 g of a product which contains 6.2% of the free isocyanate groups and which shows the typical hydantoin absorption bands at 1700 and 1755 $cm^{-1}$ in the IR spectrum are obtained. The chlorine content is 0.5%.

EXAMPLE 26

51.0 g of 4,4'-diisocyanatodiphenylmethane are added to 0.049 g of ferric acetylacetonate in 250 g of m-cresol at 100°C at a rate adjusted to the exothermic reaction, and 67.4 g of 2,3-dichlorosuccinic acid dianilide are then added at 160°C. The reaction mixture is then immediately heated to about 185°C and kept at this temperature for about 15 hours, until evolution of HCl ceases, and anhydrous nitrogen is passed through at the same time. About 353 g of an approximately 30% cresolic polyhydantoin solution which shows the characteristic IR absorption bands at 1700 and 1755 $cm^{-1}$ and has a viscosity of 2 728 $cP_{20°C}$ are obtained. The chlorine content is below 0.2%.

EXAMPLE 27

Using the method described in Example 26, 75.0 g of 4,4'-diisocyanatodiphenylmethane are added to a mixture of 0.059 g of ferric acetylacetonate in 300 g of m-cresol at 100°C, and 67.4 g of 2,3-dichlorosuccinic acid dianilide are then added at 160°C. The reaction mixture is then kept at 185°C for 15 hours while anhydrous nitrogen is passed through it.

Approximately 427 g of an oligohydantoin solution which has a concentration of about 30%, based on the free isocyanate content are obtained. The hydantoin structure of the solution is confirmed by the characteristic IR absorption bands at 1700 and 1755 $cm^{-1}$. The viscosity of the cresolic solution is 3 400 $cP_{20°C}$ and its chlorine content is below 0.2%. Titration of the masked isocyanate groups shows that the solution contains 1.7% of available NCO groups.

EXAMPLE 28

127.5 g of 4,4'-diisocyanatodiphenylmethane are added to a solution of 74.12 g of n-butanol and 0.140 g of ferric acetylacetonate in 700 g of m-cresol at 100°C at a rate adjusted to the exothermic reaction. When the NCO band has disappeared, 176.6 g of 4,4'-bis-α-chloroacetamidodiphenyl ether are added at 120°C. The reaction mixture is then immediately heated to 190° – 195°C and the quantity of alcohol introduced and the expected quantity of HCl are driven off at this temperature in the course of about 20 hours while anhydrous nitrogen is passed through.

About 968 g of an approximately 29% cresolic polyhydantoin solution which shows the characteristic IR absorption bands at 1700 and 1755 $cm^{-1}$ and has a viscosity of 2394 $cP_{20°C}$ are obtained. The chlorine content is below 0.2%.

After further dilution of the resulting brown, viscous solution with cresol, the polyhydantoin can be directly applied from it to a metal sheet and stoved to a clear lacquer film in stages at 200°C and 250°C.

EXAMPLE 29

23.0 g of ethyl alcohol and 127.5 g of 4,4'-diisocyanatodiphenylmethane in 650 g of m-cresol are kept at 80° to 90°C until the isocyanate groups have reacted. 176.6 g of 4,4'-bis-α-chloroacetamido-diphenylether are then added at 120°C and the reaction mixture is immediately heated to 190° – 195°C. It is then kept at this temperature until termination of the condensation reaction, anhydrous nitrogen being passed through it at the same time. The alcohol and HCl are driven off. About 918 g of an approximately 30% cresolic polyhydantoin solution which shows the typical IR absorption bands at 1700 and 1755 $cm^{-1}$ are obtained after about 18 hours. The viscosity of the solution is 7420 $cP_{20°C}$, its chlorine content below 0.2%.

EXAMPLE 30

A mixture of 7.5 g of n-butanol and 176.6 g of 4,4'-bis-α-chloroacetamido-diphenylether is added to 127.5 g of 4,4'-diisocyanatodiphenylmethane in 650 g of m-cresol at 120°C. The reaction mixture is kept at 120°C for 1 hour, 195°C for 10 hours and 210°C for 5 hours, anhydrous nitrogen being passed through the solution at the same time. The expected quantities of alcohol and HCl are driven off.

The resulting hydantoin ring structure is demonstrated by the presence of the typical IR absorption bands at 1700 and 1755 $cm^{-1}$. The chlorine content of the solution is below 0.2%.

We claim:

1. A process for the preparation of a compound containing hydantoin groups which comprises reacting at a temperature of 50° to 350°C. at least one compound of the formula $$R^3(-NCX)_z$$

wherein X is O or S; z is an integer of from 2 to 3 and $R^3$ is an optionally substituted aliphatic radical having 1–20 carbon atoms, an optionally substituted aromatic radical having 5–12 carbon atoms, a cycloaliphatic radical having 5–12 carbon atoms, an aliphatic-aromatic radical having 6–20 carbon atoms, an aromatic or cycloaliphatic heterocyclic radical containing 5–12 carbon atoms which contains or is substituted by hetero atoms such as N, O or S with (b) at least one α-halocarboxylic acid amide selected from the group consisting of

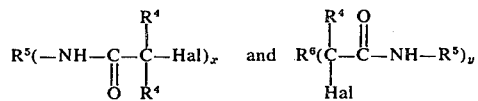

wherein Hal denotes halogen; $R^4$ is an optionally substituted aromatic radical having 5–10 carbon atoms, an aliphatic radical having 1–20 carbon atoms, a cycloaliphatic radical having 5–10 carbon atoms, hydrogen or the two radicals $R^4$ taken together with the carbon atom to which they are attached form a cycloaliphatic ring of 5–7 ring members, $R^5$ is one of the radicals defining $R^3$; $R^6$ is an aliphatic radical having 1–10 carbon atoms, a cycloaliphatic radical having 5–10 carbon atoms, an aliphatic-aromatic radical having 6–10 carbon atoms or an aromatic radical having 5–10 carbon atoms and $x$ and $y$ are integers from 2 to 3.

2. The process as claimed in claim 1 wherein 1 mol of (a) is reacted with from 2/z to 4/z mol of (b).

3. The process as claimed in claim 1 wherein 1 mol of (a) is reacted with 2/z mol of (b).

4. The process as claimed in claim 1 wherein 1 mol of (a) is reacted with 4/z mol of (b).

5. The process as claimed in claim 1 wherein the reaction is carried out in a phenolic solvent or in the presence of an aliphatic alcohol or polyol.

6. The process as claimed in claim 1 wherein the reaction is carried out in the presence of at least one organic metal compound of iron, lead or tin or in the presence of iron chloride, lead oxide or lead carbonate.

7. The process as claimed in claim 1 wherein the reaction is carried out in the presence of a tertiary amine.

8. The process as claimed in claim 1 wherein (a) is tolylene diisocyanate, m-phenylenediisocyanate, polyphenylenemethylene-polyisocyanate, 4,4-diisocyanato-diphenylmethane, 4,4-diisocyanato-diphenylether, 4,4-diisocyanato-diphenyldimethylmethane, p-phenylene diisocyanate or hexamethlyene diisocyanate.

9. The process as claimed in claim 1 wherein up to 100% of the isocyanate groups are present in the O-alkylurethane form.

10. The process as claimed in claim 1 wherein (b) is the amide of chloroacetic acid, α-chlorinated or α-brominated propionic, butyric, 2-ethylhexanoic, stearic, phenylacetic, diphenylacetic, dimethylacetic, isopropylacetic or cyclohexanoic acid or α,α'-chlorinated or α,α'-brominated succinic, adipic, glutaric, sebacic or phenylene diacetic acid.

* * * * *